(12) United States Patent
Thudor et al.

(10) Patent No.: US 7,111,624 B2
(45) Date of Patent: Sep. 26, 2006

(54) APPARATUS FOR DELIVERING HUMIDIFIED GASES

(75) Inventors: Mohammad Thudor, Auckland (NZ); Ian Douglas Makinson, Auckland (NZ); Philip James Biggs, Auckland (NZ); Philip John Dickinson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 518 days.

(21) Appl. No.: 10/246,328

(22) Filed: Sep. 18, 2002

(65) Prior Publication Data

US 2003/0066526 A1 Apr. 10, 2003

Related U.S. Application Data

(63) Continuation-in-part of application No. 09/808,567, filed on Mar. 14, 2001, now Pat. No. 6,918,389.

(30) Foreign Application Priority Data

Mar. 21, 2000 (NZ) ...................................... 503495

(51) Int. Cl.
*A61M 15/00* (2006.01)
*A62B 7/00* (2006.01)

(52) U.S. Cl. ........................ 128/203.16; 128/204.17; 128/204.18; 128/203.17

(58) Field of Classification Search ........... 128/203.12, 128/203.17, 203.16, 203.26, 203.27, 204.17; 604/23; 392/386, 390; 261/DIG. 65, DIG. 4, 261/DIG. 515
See application file for complete search history.

(56) References Cited

U.S. PATENT DOCUMENTS

| 485,127 | A | 10/1892 | Lynch |
|---|---|---|---|
| 3,582,968 | A | 6/1971 | Buiting |
| 3,584,193 | A | 6/1971 | Badertscher |
| 3,695,267 | A | 10/1972 | Hirtz et al. |
| 3,766,914 | A | 10/1973 | Jacobs |
| 3,914,349 | A | 10/1975 | Stipanuk |
| 4,013,122 | A | 3/1977 | Long |
| 4,013,742 | A | 3/1977 | Lang |
| 4,038,980 | A | 8/1977 | Fodor |
| 4,060,576 | A | 11/1977 | Grant |
| 4,110,419 | A | 8/1978 | Miller |
| 4,172,105 | A | 10/1979 | Miller et al. |
| 4,500,480 | A | 2/1985 | Cambio, Jr. |
| 4,574,188 | A | 3/1986 | Midgley et al. |
| 4,640,804 | A | 2/1987 | Mizoguchi |

(Continued)

FOREIGN PATENT DOCUMENTS

DE 3311811 10/1984

(Continued)

*Primary Examiner*—Glenn K. Dawson
(74) *Attorney, Agent, or Firm*—Trexler, Bushnell, Giangiorgi, Blackstone & Marr, Ltd.

(57) ABSTRACT

An apparatus for delivering humidified gases has a connection manifold adapted to connect with inlet and outlet ports of a slide on water chamber in a single slide on motion. Connection of the gases inlet and gases outlet ports as well as any additional electrical and/or pneumatic connections are all made in the same slide on motion. The water chamber may include inwardly extending elongate extension tubes with one of the extension tubes having an air bleed aperture to aid filling of the chamber.

7 Claims, 7 Drawing Sheets

U.S. PATENT DOCUMENTS

| | | | |
|---|---|---|---|
| 4,676,237 A | 6/1987 | Wood et al. | |
| 4,684,786 A | 8/1987 | Mann et al. | |
| 4,710,887 A | 12/1987 | Ho | |
| 4,722,334 A | 2/1988 | Blackmer et al. | |
| 4,753,758 A | 6/1988 | Miller | |
| 4,780,247 A | 10/1988 | Yasuda | |
| 4,829,998 A | 5/1989 | Jackson | |
| 4,911,157 A | 3/1990 | Miller | |
| 4,911,357 A | 3/1990 | Kitamura | |
| 4,921,642 A * | 5/1990 | LaTorraca | 261/142 |
| 4,941,469 A | 7/1990 | Adahan | |
| 5,031,612 A | 7/1991 | Clementi | |
| 5,062,145 A | 10/1991 | Zwaan et al. | |
| 5,092,326 A | 3/1992 | Winn et al. | |
| 5,101,820 A | 4/1992 | Christopher | |
| 5,148,801 A | 9/1992 | Douwens et al. | |
| 5,224,923 A | 7/1993 | Moffett et al. | |
| 5,231,979 A * | 8/1993 | Rose et al. | 128/204.14 |
| 5,336,156 A | 8/1994 | Miller et al. | |
| 5,346,128 A | 9/1994 | Wacker | |
| 5,367,604 A | 11/1994 | Murray | |
| 5,388,443 A | 2/1995 | Manaka | |
| 5,392,770 A | 2/1995 | Clawson et al. | |
| 5,404,729 A | 4/1995 | Matsuoka et al. | |
| 5,454,061 A | 9/1995 | Carlson | |
| 5,482,031 A | 1/1996 | Lambert | |
| 5,516,466 A * | 5/1996 | Schlesch et al. | 261/117 |
| 5,529,060 A | 6/1996 | Salmon et al. | |
| 5,558,084 A | 9/1996 | Daniell et al. | |
| 5,564,415 A * | 10/1996 | Dobson et al. | 128/204.14 |
| 5,588,423 A | 12/1996 | Smith | |
| 5,640,951 A | 6/1997 | Huddart et al. | |
| 5,673,687 A | 10/1997 | Dobson et al. | |
| 5,759,149 A | 6/1998 | Goldberg et al. | |
| 5,769,071 A | 6/1998 | Turnbull | |
| 5,988,164 A | 11/1999 | Paluch | |
| 5,991,507 A * | 11/1999 | Bencsits | 392/395 |
| 6,024,694 A | 2/2000 | Goldberg et al. | |
| 6,050,260 A | 4/2000 | Daniell et al. | |
| 6,078,730 A | 6/2000 | Huddart et al. | |
| 6,095,505 A | 8/2000 | Miller | |
| 6,125,847 A | 10/2000 | Lin | |
| 6,158,431 A | 12/2000 | Poole | |
| 6,311,958 B1 | 11/2001 | Stanek | |
| 6,349,722 B1 | 2/2002 | Gradon et al. | |
| 6,367,472 B1 | 4/2002 | Koch | |
| 6,394,084 B1 | 5/2002 | Nitta | |
| 6,397,846 B1 | 6/2002 | Skog et al. | |
| 6,398,197 B1 * | 6/2002 | Dickinson et al. | 261/141 |
| 6,463,925 B1 | 10/2002 | Nuckolas et al. | |
| 6,474,335 B1 | 11/2002 | Lammers | |
| 6,543,412 B1 | 4/2003 | Amou et al. | |
| 6,564,011 B1 | 5/2003 | Janoff et al. | |
| 6,694,974 B1 | 2/2004 | George-Gradon et al. | |
| 6,718,974 B1 * | 4/2004 | Moberg | 128/204.14 |
| 2002/0124847 A1 | 9/2002 | Smith et al. | |

FOREIGN PATENT DOCUMENTS

| | | | |
|---|---|---|---|
| DE | 3629353 | 1/1988 | |
| DE | 4034611 | 5/1992 | |
| DE | 94092311 | 11/1994 | |
| EP | 0258928 | 9/1988 | |
| EP | 481459 | 4/1992 | |
| EP | 556561 | 8/1993 | |
| EP | 0672430 | 9/1995 | |
| EP | 0885623 | 12/1998 | |
| EP | 1138341 | 10/2001 | |
| GB | 1167551 | 10/1969 | |
| GB | 2277689 | 11/1994 | |
| JP | 05317428 | 12/1993 | |
| JP | 08061731 | 8/1996 | |
| JP | 09234247 | 9/1997 | |
| JP | 2001-129091 * | 5/2001 | 128/204.14 |
| SU | 379270 | 4/1973 | |
| WO | WO 9826826 | 6/1998 | |
| WO | 01/10489 * | 2/2001 | 128/204.14 |
| WO | WO 0110489 | 2/2001 | |
| WO | WO 02/32486 | 4/2002 | |

\* cited by examiner

APPARATUS FOR DELIVERING HUMIDIFIED GASES

This is a Continuation-In-Part of U.S. patent application Ser. No. 09/808,567 filed on Mar. 14, 2001 now U.S. Pat. No. 6,918,389.

BACKGROUND TO THE INVENTION i) Field of the Invention

The present invention relates to apparatus for delivering humidified gases. In particular it relates to a humidifier arrangement for use in stand alone humidifiers used for example in providing respiratory assistance to patients receiving mechanical ventilation or respiratory support and/or integrated humidifiers included for example in consumer CPAP delivery devices.

ii) Summary of the Prior Art

Humidification systems are known which include a heater base and a disposable humidifier chamber which is fitted onto the heater base and within which a supply of water can be heated by the heater base. Air enters the humidifier chamber through an inlet air port in the roof of the chamber where it is humidified by the evaporation of water from the water supply before leaving the chamber through an exit port in the roof of the humidifier chamber.

Humidifier chambers of this type are also now used in compact and portable ventilation machines, for example machines intended for the home treatment of obstructive sleep apnoea (CPAP machines). Where the humidifier base is adapted for use with slide-on humidifier chambers, and the connection of the chamber to the machine is accomplished with a single sliding movement, the inlet air port is provided horizontally through the side of the chamber. Air enters the humidifier chamber through the inlet air port and the humidified air leaves the humidifier chamber into a breathing conduit through an exit port in the top of the humidifier chamber.

A disadvantage of these configurations is the need to disconnect the patient breathing conduit from the top of the humidifying chamber in a separate operation before removal of the chamber for the purpose of refilling. A further disadvantage of these configurations is that separate electrical wiring connections are required to make use of a heated respiratory conduit.

SUMMARY OF THE INVENTION

It is an object of the present invention to provide an apparatus for delivering humidified gases which at least goes some way towards overcoming the above disadvantages or which will at least provide the public with a useful choice.

In a first aspect the invention consists in an apparatus for use in humidified gases delivery treatment comprising:

a housing, a pressurised gases outlet in said housing adapted to make fluid connection with an inlet of a humidifier in order to provide gases flow to a said humidifier, a humidified gases return in said housing, adapted to make fluid connection with an outlet of a said humidifier in order to receive humidified gases from said humidifier, a patient outlet in said housing, in fluid connection with said humidified gases return in order to receive humidified gases from said humidified gases return and provide humidified gases to said patient outlet, said patient outlet being in fluid connection with or adapted to make fluid connection with a breathing conduit for delivery of humidified gases to a patient.

In a further aspect the invention consists in an apparatus for use in humidified gases delivery treatment comprising:

a housing, a pressurised gases supply within said housing, a pressurised gases outlet in said housing in fluid connection with said pressurised gases supply and adapted to make fluid connection with an inlet of a humidifier in order to provide gases flow to a said humidifier, a humidified gases return in said housing, adapted to make fluid connection with an outlet of a said humidifier in order to receive humidified gases from said humidifier, a patient outlet in said housing, in fluid connection with said humidified gases return in order to receive humidified gases from said humidified gases return and provide humidified gases to said patient outlet, said patient outlet being in fluid connection with or adapted to make fluid connection with a breathing conduit for delivery of humidified gases to a patient.

In a still further aspect the invention consists in an apparatus for use in humidified gases delivery treatment comprising:

a housing, a gases line inlet in said housing to receive pressurised gases from a pressurised gases source, said gases line inlet adapted to make fluid connection with a breathing conduit, a gases outlet in said housing in fluid connection with said gases line inlet, adapted to make fluid connection with an inlet of a humidification chamber in order to provide gases flow into a said humidification chamber, a humidified gases return in said housing, adapted to make fluid connection with an outlet of a said humidification chamber in order to receive humidified gases from said humidification chamber, a gases line outlet in said housing, in fluid connection with said humidified gases return, adapted to make fluid connection with a breathing conduit for delivery of humidified gases to a patient, a chamber heating means in said housing for vaporising liquid water in said humidification chamber in order to provide water vapour to gases flow passing through said humidification chamber, said humidification chamber having a base, said chamber being removable and engagable with said housing via a single motion, said single motion of engagement urging the base of said humidification chamber adjacent and in contact with said chamber heating means, and making a first fluid connection between said gases outlet and said humidification chamber inlet, and making a second fluid connection between said humidified gases return and said humidification chamber outlet, said first and second fluid connections being made in the direction of said single motion.

In a still further aspect the invention consists in a humidifier chamber for use with a gases humidification apparatus comprising:

a container, with a surrounding wall and top, and an open bottom, a heat conductive base enclosing said open bottom of said container, a gases inlet to said container, a gases outlet to said container, said gases inlet and said gases outlet facing the same direction, not being upwards, such that said humidifier chamber may make operable engagement with a heater base in a single motion, and fluid connections with said gases outlet and said gases inlet, being also made in said single motion.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

Two preferred embodiments of the present invention will now be described with reference to the drawings.

DETAILED DESCRIPTION

Two preferred embodiments of the present invention will now be described in detail.

Figure 1:
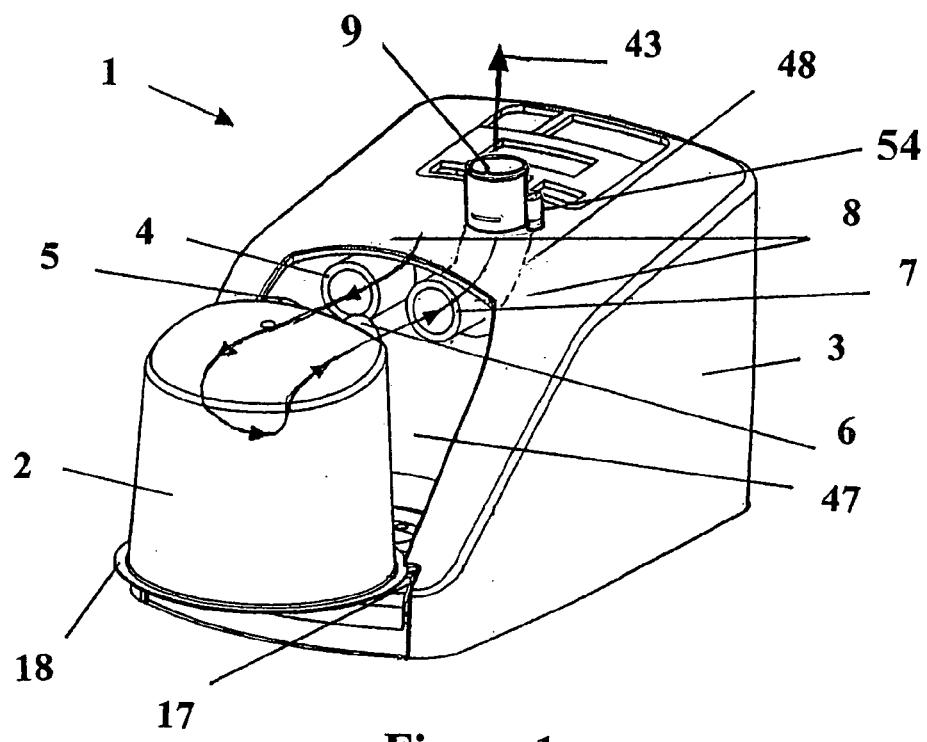
FIG. 1 is a perspective view of a water chamber and CPAP machine according to the first preferred embodiment of the present invention showing the water chamber 2 separated from the CPAP machine 1 and an arrow 43 indicating the path of air flow through the connection manifold of the CPAP machine and chamber.
Figure 2:
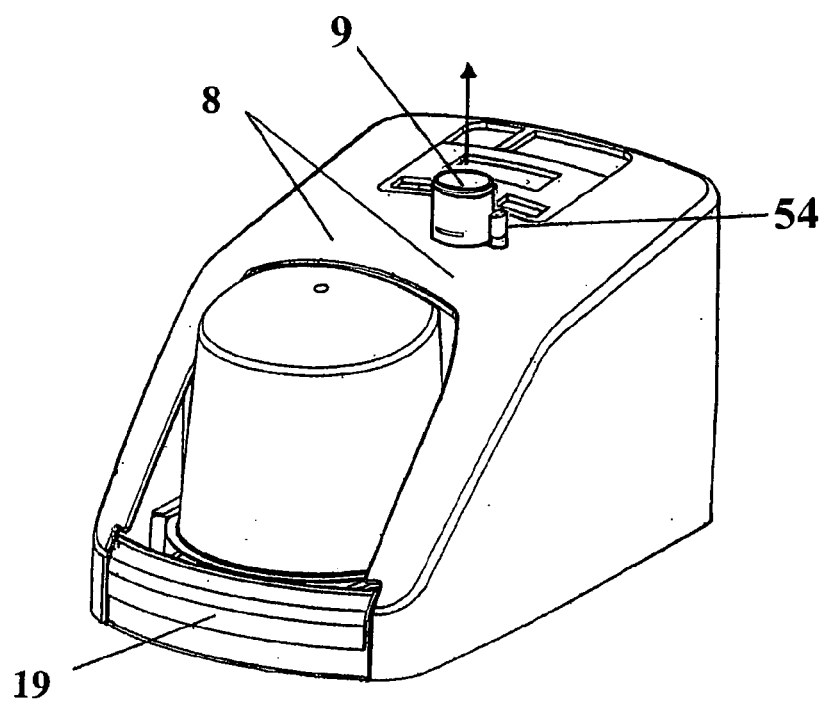
FIG. 2 is a perspective view of a water chamber and CPAP machine according to the first preferred embodiment of the present invention showing the water chamber 2 engaged with the CPAP machine 1 as in use and an arrow indicating the exit path of air flow through the conduit connection manifold 9.

Referring to FIGS. 1 and 2, a first preferred embodiment of a CPAP machine and corresponding water chamber is shown. A water chamber having a gases inlet port 5 and gases outlet port 6 is shown with a portable CPAP machine, wherein the CPAP machine is adapted to receive slide-on chambers and which makes connection to the gases inlet/outlet ports of the water chamber through a connection manifold. Connection of the gases inlet and gases outlet ports are made to the connection manifold 8 of the CPAP machine in the same slide-on motion. The connection manifold also provides an auxiliary outlet connection port 9 suitable for receiving a flexible respiratory conduit to deliver humidified air to a patient.

The CPAP machine includes a heater base in a chamber receiving bay 47 to heat the water chamber, and a securing means for securing the water chamber to the CPAP machine. The securing means is provided by a securing latch 19 and a slot 17 around the periphery and of the chamber receiving bay 47. The slot co-operates with a flange 118 around the base of the water chamber to secure the chamber when in use. The securing latch 19 operates to prevent removal of the chamber once it has been engaged. The securing means and connection manifold are arranged with a parallel axis of operation such that connection of the chamber inlet and outlet ports 5 & 6, to the connection manifold 8 is achieved as well as securing of the chamber into the CPAP machine in the same slide-on motion.

The latch 19, having a locking position and a release position, is biased toward the locking position which prevents removal of the chamber from the CPAP machine. The front face of the latch is shaped such that during the single slide-on motion employed to fit the water chamber to the CPAP machine the flange 18 urges the securing latch 19 into the release position and allows the water chamber to be properly fitted. Once the water chamber is properly seated on the heater base and the inlet 5 and outlet 6 is properly engaged with the connection manifold 8, the flange 18 and base of the chamber will no longer be in contact with the securing latch 19. This allows the securing latch biasing means to urge the latch into the locking position and prevent the water chamber from being removed as shown in FIG. 2.

Preferably the connection manifold 8 includes a passage which receives airflow from the blower and directs it into the water chamber 2, as well as a passage which directs airflow received via the water chamber outlet port 6, to the CPAP patient outlet port 9. The connection passage connecting the manifold inlet port 7, to the manifold patient outlet port 9 is shown in hidden detail 48 in FIG. 1. Preferably the connection manifold 8 of the present invention is removable to aid cleaning and/or sterilisation of the passages. In one preferred embodiment the above connection passages are internal to the connection manifold 8 as illustrated in FIGS. 1 and 2.

In use air from the CPAP machine blower exits through outlet port 4, and enters the chamber 2 through inlet port 5. Air entering the chamber is humidified by the evaporation of water from the water source in the bottom of the chamber before leaving the chamber through the patient outlet port 6. Humidified air from the outlet port 6 is received into the connection manifold of the CPAP machine 9 via the inlet port 7. The connection manifold 8 directs air to the outlet port 9 which is adapted to connect with a flexible conduit connector for delivery to a patient. An advantage obtained from the breathing conduit connection 9 being located on the body of the CPAP machine and not connected to the top of the water chamber directly, is that complete connection or disconnection of the water chamber from the CPAP system can be achieved with a single slide-on or slide-off motion. This feature makes removal of the water chamber for refilling considerably simpler.

A further advantage is obtained when additional electrical or pneumatic connections are required. The use of heated conduits requires electrical wiring connectors between the conduit and humidified air source while an additional pneumatic connection may be used for pressure feedback or measurement. In the present invention the connector which includes an additional electrical and/or pneumatic connection 54 for the conduit is integral to the connection manifold of the CPAP machine 8 and therefore allows the disposable water chamber to remain as simple as possible.

Figure 3:
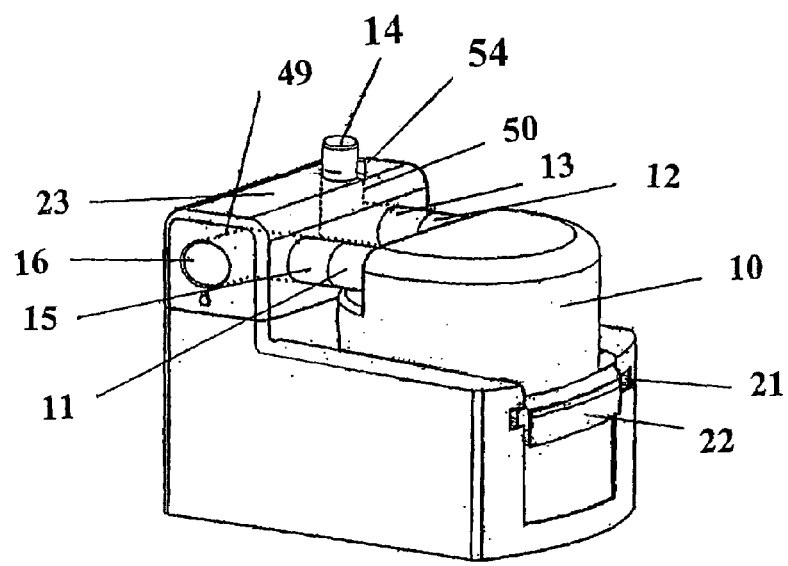
FIG. 3 is a perspective view of a water chamber and humidifier base according to the second preferred embodiment of the present invention showing the water chamber 10 engaged in the connection manifold 23 of the heater base as in use.

Referring to FIG. 3, a second preferred embodiment of an in-line humidifier and corresponding water chamber is shown. A water chamber having a gases inlet port 11 and gases outlet port 12 is shown with an in line humidifier, wherein the humidifier is adapted to receive slide-on chambers and which makes connection to the gases inlet/outlet ports of the water chamber through a connection manifold 23. Connection of the gases inlet and gases outlet port is made through the connection manifold 23 of the humidifier in the same slide-on motion. The connection manifold has an auxiliary inlet port 16 suitable for connection of a flexible conduit for delivery of airflow to the humidifier and an auxiliary patient outlet port 14 suitable for receiving flexible respiratory conduits to receive the humidified air flow.

Preferably the connection manifold 23 includes a passage 49 which receives airflow from the inlet conduit through inlet port 16 and directs it into the water chamber inlet port 11 through manifold outlet port 15. Preferably the connection manifold 23 also includes a passage 50 which receives airflow from the water chamber outlet port 12, via manifold inlet port 13 and directs it to the manifold patient outlet port 14. The connection passages 49 and 50 are shown in hidden in FIG. 3. Preferably the connection manifold 23 of the present invention is removable to aid cleaning and/or sterilisation of the passages. Preferably the connection passages are internal to the connection manifold 23.

The humidifier includes a heater base to heat the water chamber and a securing means for securing the water chamber to the humidifier. The securing means is provided by a securing latch 22 and a slot 21 around the periphery and of the chamber receiving bay. The slot co-operates with a flange around the base of the water chamber 10 to secure the chamber when in use, while the securing latch operates to prevent removal of the chamber once it has been engaged. The securing means and connection manifold are arranged such that connection of the chamber inlet and outlet ports 11 and 12, to the connection manifold 23 is achieved at the same time as securing of the chamber into the humidifier in the same slide-on motion. The latch 22, having a locking position and a release position, is biased toward the locking position which prevents removal of the chamber from the humidifier. The front face of the latch 22 is shaped such that during the single slide-on motion employed to fit the water chamber to the humidifier the flange urges the securing latch 22 into the release position and allows the water chamber 10 to be properly fitted. Once the water chamber is properly seated on the heater base and the inlet 11 and outlet 12 is properly engaged with the connection manifold 23, the flange and base of the water chamber will no longer be in contact with the securing latch 22 This allows the securing latch biasing means to urge the latch into the locking position and prevent the water chamber from being removed.

In use the humidifier inlet port 16 receives air flow through a flexible conduit. Air leaves the connection manifold 23 through the outlet port 15 and enters the water chamber 10 through the chamber inlet port 11, where it is humidified by the evaporation of water from the water supply. Humidified air leaves the water chamber via outlet port 12, enters the humidifier connection manifold inlet port 13, finally exiting through the patient outlet port 14 into a breathing conduit for delivery to a patient. An advantage obtained by having both the inlet 16 and outlet 14 which connect to conduits, integral to the body of the humidifier and not part of the water chamber directly, is that complete connection/disconnection of the water chamber 10 from the humidifier base can be achieved with a single slide-on/off motion. This feature makes removal of the water chamber for refilling considerably simpler.

In a similar manner to the first preferred embodiment of a CPAP machine, a further advantage obtained from the configuration of the second preferred embodiment, arises when an additional electrical or pneumatic connection is required. The inlet and/or outlet connectors including an electrical and/or pneumatic connection 54 for the conduit are integral to the connection manifold of the humidifier and therefore allow the disposable water chamber to remain as simple as possible.

Figure 4:
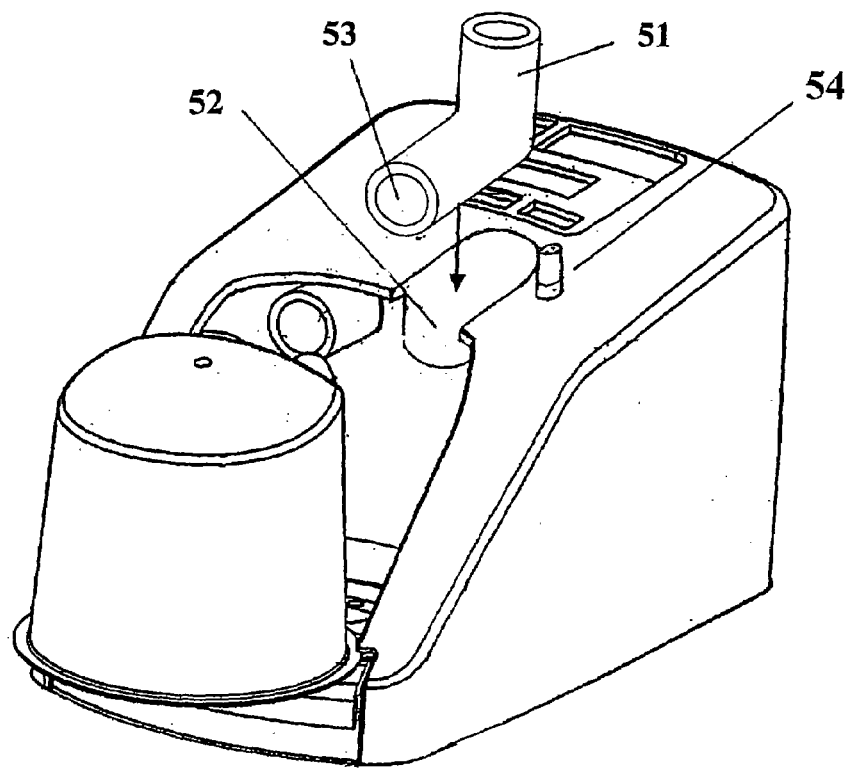
FIG. 4 is a perspective view of a CPAP machine and water chamber according to an alternative embodiment of the present invention.

A number of alternative variations of the first and second preferred embodiments are envisaged and will now be described. For example, a further embodiment of the present invention is envisaged to deliver humidified gases from the water chamber to a patient via a flexible breathing conduit. This alternative embodiment is shown in FIG. 4. An elbow tube 51 having an inlet end and an outlet end is provided to receive humidified gases from the water chamber and direct humidified gases into a flexible breathing condiut for delivery to a patient. In this alternative preferred embodiment the CPAP machine housing is provided with a recess 52 for receiving and securing the elbow tube. For example the recess 52 may include a neck or constriction that is above the elbow 51 when elbow 51 is in place. The neck holds the elbow in place under normal usage, but the elbow can be forcibly removed when required. When secured in position, an inlet 53 of the elbow tube 51 is positioned to make a fluid connection to the outlet 6 of the water chamber in the same slide on motion. In this alternative embodiment the outlet elbow may be part of the termination of the breathing tube instead of an internal part of the connection manifold as previously described. An advantage of this alternative embodiment is that all the parts in contact with condensation are removable for cleaning or sterilisation. This embodiment also retains the advantage of an engagable/disengagable water chamber in a single slide on/off motion. This embodiment may also include additional electrical or pneumatic connections 54 for making a connection between the CPAP machine and a conduit connector, enabling this alternative to retain the advantages of the previously described embodiments. While FIG. 4 shows this alternative preferred embodiment of the present invention applied to a CPAP machine it is envisaged that this embodiment may also be applied in an analogous manner to an inline humidifier such as that described in the second embodiment of the present invention and pictured in FIG. 3.

An alternative embodiment of the present invention is envisaged wherein a water chamber and heater base are partially or fully enclosed in a housing. The housing includes a connection manifold consisting of at least one gases inlet and at least one gases outlet connection port being adjacent and aligned, which in use transport gases to and/or from the water chamber. A second housing is provided with complementary inlet and outlet connections for registration with the connection manifold. The second housing is adapted to engage with the first housing making all the necessary gases and electrical connections in the same slide-on motion and preferably includes a securing means. The second housing may include an integral air blower, and a patient conduit outlet port in the case of a CPAP embodiment. Or in the case of an in-line humidifier embodiment, the second housing may include two conduit ports. The first conduit port in use receiving air from a source and the second conduit port delivering humidified air to a patient. The above described embodiment has the advantage hat all necessary flexible conduit connections are made on the second housing. This enables the water chamber and/or enclosing housing to be removed/engaged in the same slide-off/on motion making refilling of the chamber simpler.

In the first and second preferred embodiments of the present invention, tubular protrusions are provided for making a connection between the humidifier apparatus and a water chamber in order to deliver gases to the chamber and receive humidified gases from the chamber. Preferably the tubular protrusions also include a resilient boot in order to provide an improved seal between the water chamber and the protrusions.

A further embodiment of the present invention is envisaged wherein the connections between the apparatus manifold and the water chamber are not provided side by side as described in the first and second embodiment of the present invention but rather are provided one within the other, for example the inlet and outlet may be coaxial. Such a configuration would enjoy the same advantages as the configurations described in more detail in the first and second embodiments of the present invention. It is also envisaged that such connections may also include similarly configured tubes for providing pressure measurements or pressure feedback.

While the above preferred embodiments describe male/female type connectors wherein the water chamber has two female connectors for mating with corresponding male connectors of the apparatus manifold, it is envisaged that many variations will present themselves to those skilled in the art without departing from the spirit of the present invention. For example the water chamber may be provided with two male connectors while the apparatus manifold is provided with corresponding female connectors, or the water chamber may be provided with one male and one female connector for connecting to the corresponding male and female connectors of the apparatus manifold. Further it is envisaged that connectors of an androgynous nature may be provided for making connection between the water chamber and the apparatus manifold wherein each connector may include both male type protruding portions and female type recess portions. Such connections may be particularly advantageous when the inlet and outlet is provided one within the other.

With reference to the first and second preferred embodiments of the present invention, some common features of a water chamber suitable for use with either preferred embodiment will now be described in more detail.

Figure 5:
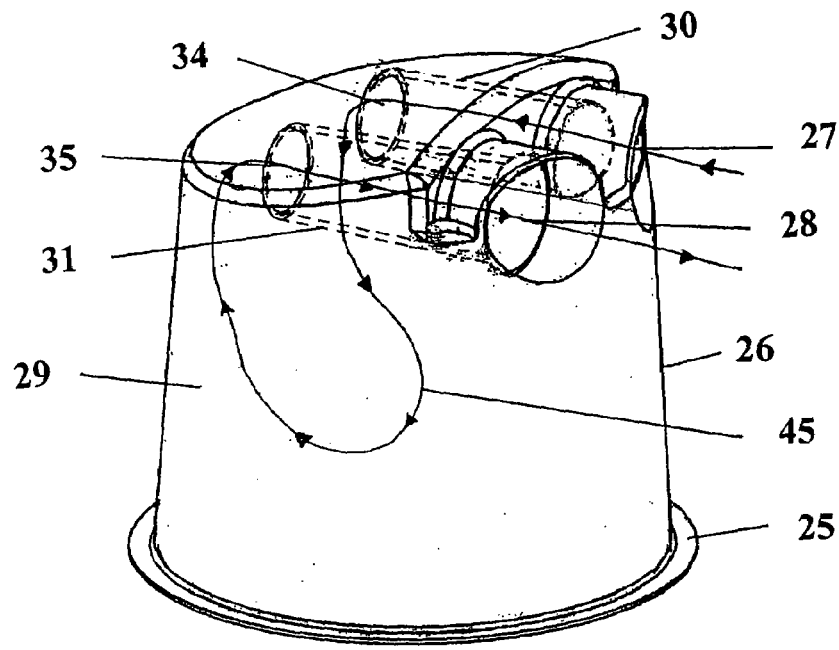
FIG. 5 is a perspective view of a water chamber of the present invention showing hidden detail of the inlet and outlet extension tubes.

The chamber as shown in FIG. 5 is constructed from an open bottomed plastic container enclosed by a heat conductive base 24, and includes a horizontally aligned gases inlet 27 and a parallel gases outlet 28. It is envisaged that other configurations of the present invention are possible where the slide-on direction employed to fit the water chamber is not horizontal but at an angle from the horizontal or vertical. In such cases, the gases inlet 27 and outlet 28, are preferably parallel and aligned with the direction of the intended slide-on motion to allow mating of the chamber inlet/outlet ports and the connection manifold.

Figure 6:
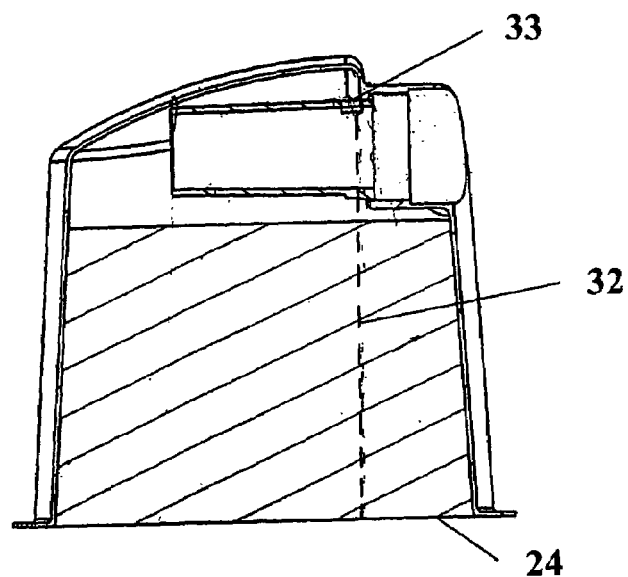
FIG. 6 is a sectioned side view of the water tube of FIG. 5 section through a mid-line of the outlet extension tube with the intended water level shown hatched.

The water chamber of the present invention preferably includes an inlet extension tube 30, and an outlet extension tube 31, extending inwardly into the chamber interior from the periphery of the chamber wall and preferably having a generally tapering body. The inlet extension tube 30 and the outlet extension tube 31 are preferably moulded from the same clear thermoplastic material as the chamber shell 26. The inclusion of inlet/outlet extension tubes has been found to significantly reduce noise produced by the airflow around the chamber. Preferably at least one extension tube has an air bleed aperture to aid filling of the chamber with the chamber tipped up. The air bleed is preferably located in the top surface of the extension tube and preferably toward the end of the extension tube which is connected to the chamber wall. Referring to FIG. 6, preferably the air bleed aperture 33 is positioned such that when the tank is tipped up for filling, the air bleed valve height corresponds with the preferred fill height 32 for the water chamber. This feature aids in preventing overfilling of the water chamber.

Figure 7:
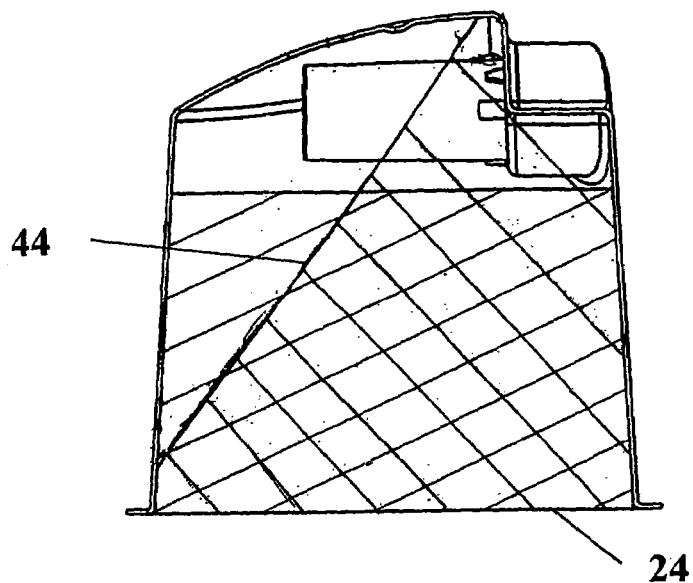
FIG. 7 is a sectioned side view of the water chamber of FIG. 5 sectioned through a mid-line of the chamber with the water level of the chamber when tilted shown hatched.

Additionally, with reference to FIG. 7, the extension tubes 30 and 31 may act as a weir against water flow back through the gases inlet and gases outlet, upon tilting of the chamber as shown by water level line 44. If present, preferably the air bleed aperture 33 is present only on the outlet extension tube 31 and not present in the inlet extension tube 30. This prevents water back-flow through the inlet port 27 occurring upon tilting of the chamber.

The present invention may further include a downwardly extending central baffle or rib located between the inlet and outlet extension tubes to ensure against gases short circuiting the chamber by flowing directly from the exit of the inlet extension tube 34, to the entry of the outlet extension tube 35. With the baffle the gases are forced to follow a more tortuous path ensuring adequate humidification during their journey through the chamber.

In use air is received into the chamber via inlet port 27 and travels down the inlet extension tube 30. On exiting the inlet extension tube 30 air enters the chamber where it is humidified by the evaporation of water from the water supply. Humidified air flows from the chamber through the outlet extension tube 31 and exits through outlet port 28. The above described flow path is illustrated in FIG. 5 by the arrow 45.

Although the preceding description gives details of preferred embodiments having parallel and adjacent circular inlet/outlet ports, it is envisaged that other configurations are possible without departing from the spirit of the invention. For example the inlet/outlet ports of the chamber and connection manifold may have a noncircular cross section and not be symmetrical. Further it is possible that the position of the inlet port with respect to the outlet may take one of many alternative configurations. For example the ports and there corresponding connections may also be co-axial or off-set, one inside the other.

Figure 8:
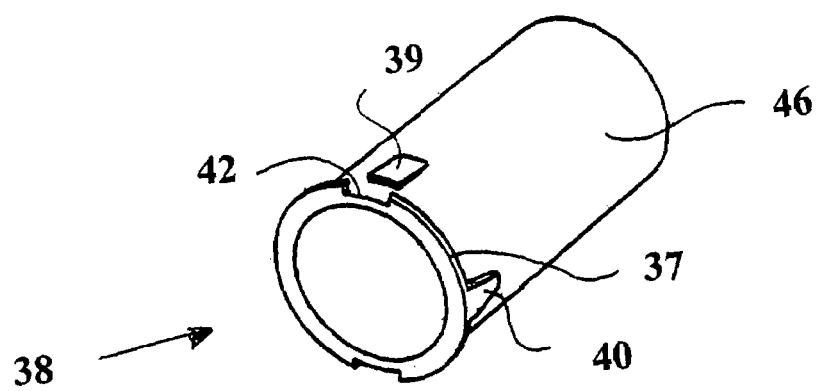
FIG. 8 is a perspective view of an inlet/outlet extension tube according a preferred embodiment of the present invention showing snap-fit protrusions and locating/locking means.
Figure 9:
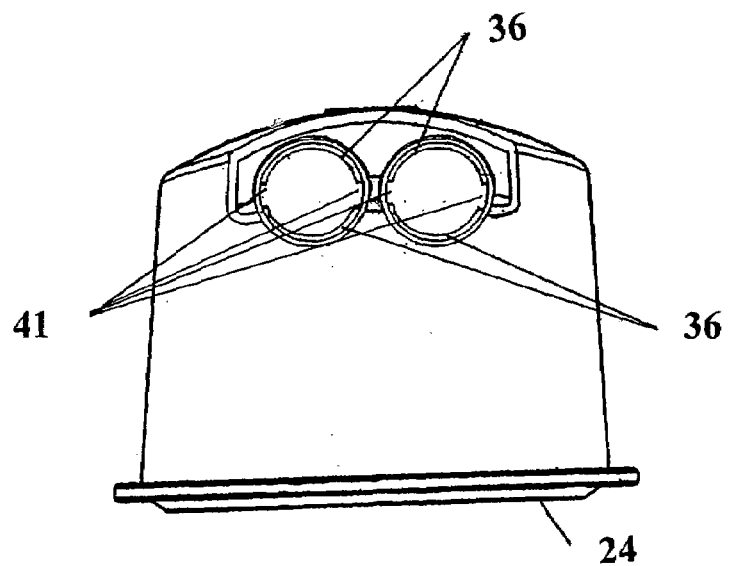
FIG. 9 is a front view of a water chamber of the present invention showing the flanges and notches which cooperate with the extension tubes detailed in FIG. 8.
Figure 10:
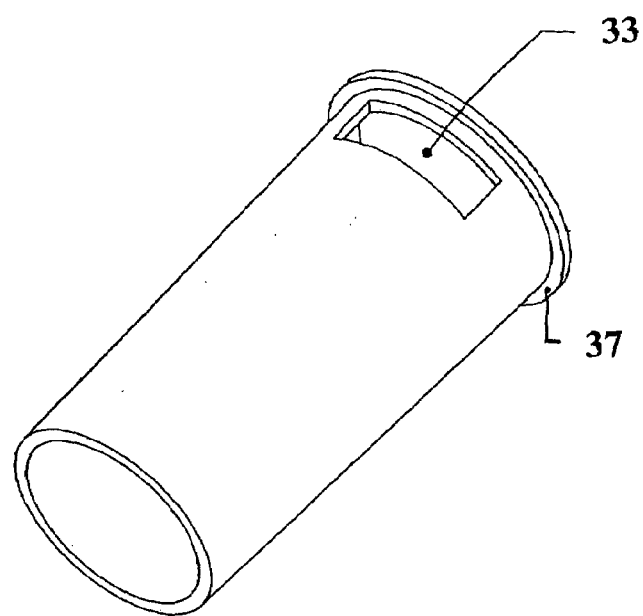
FIG. 10 is a perspective view of an outlet extension tube according to a preferred embodiment of the present invention showing the air bleed slot.
Figure 11:
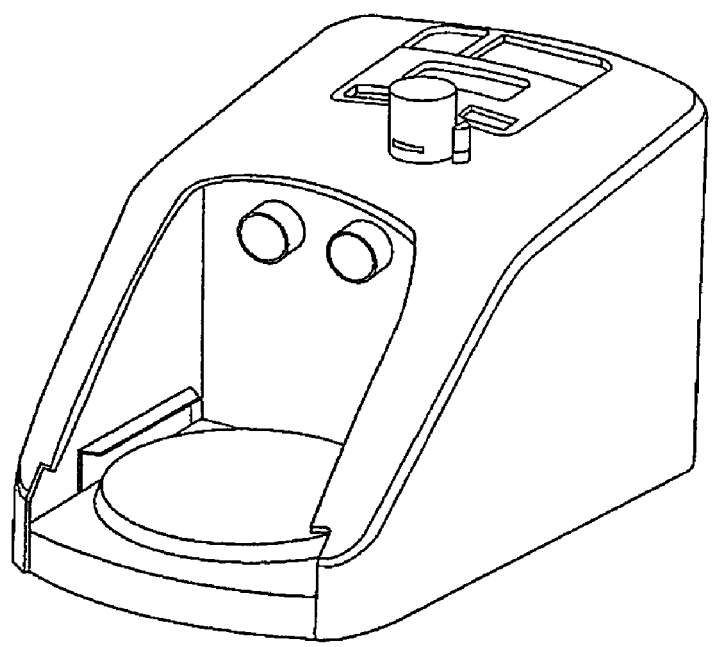
FIG. 11 is a perspective view of the CPAP machine of FIG. 2.
Figure 12:
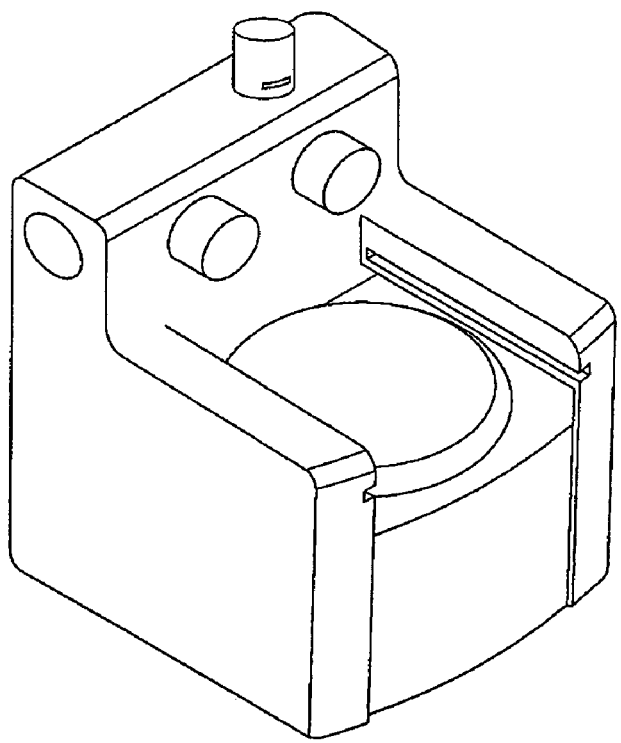
FIG. 12 is a perspective view of the humidifier base of FIG. 3.

Referring to FIGS. 8–10, for ease of assembly the inlet and outlet extension tubes are preferably provided as a snap fit to their respective water chamber inlet or outlet, so that they can be pushed into the chamber through the inlet or outlet and, upon application of sufficient force, snap into a substantially watertight and secure condition.

To this end the inlet 27 and outlet 28 ports of the water chamber may be provided with an inwardly perpendicularly extending annular flange 36 at the inner end thereof and the inlet/outlet extension tubes 38 may include similar perpendicularly outwardly extending flanges 37 from one end of the generally tapering tubular body 46. The flanges act together as sealing flanges in the fitted and assembled condition. To retain the extension tubes in the assembled condition, against both translational and rotational movement several securing mechanisms may be provided. In each case the securing mechanisms may be provided on either of the inlet/outlet (of the chamber) or the inlet/outlet extension tube. However it is preferred that they be on the extension tubes, as both components are intended for injection moulding and injection moulding of certain protrusions on the inner surface of the chamber inlet/outlet would be considerably more difficult than on the outer surface of the extension tubes. To secure the tubes against translational movement, and in a sealing condition between the sealing flanges, a plurality of retaining clip protrusions 39 may be provided spaced around the circumference of the tubular body of the extension tubes which co-operate with the inlet/outlet flange 36. Particularly for ease of manufacture, and ensuring a simple two part injection mould, a notch 42 is allowed in the flange 37 of the extension tubes 38 adjacent the protrusion 39.

To retain the extension tubes against rotational movement when snap fitted into location, one or more locating protrusions 40 may be provided circumferentially distributed on the outer surface of the tubular body adjacent and contiguous with the outwardly and perpendicularly extending flange 37. The locating protrusions 40 are preferably generally tapered in both the circumferential and axial direction. Complementary notches 41 are provided in the inwardly extending flanges 36 of the chamber inlet and outlet. In fitting the extension tubes 38 the protrusions 40 are aligned with the notches 41, and upon full insertion of the tubes, the protrusions 40 enter into a tight frictional fit with the notches 41 ensuring substantial if not complete sealing. It will be appreciated that the mechanism employed to ensure proper location and sealing of the extension tubes into the water chamber may take many forms. Many alternatives will suggest themselves to persons skilled in the art such as glued joints, various forms of plastic welding and various configurations of clipping means and protrusions. The above description is of one particular preferred embodiment and is not meant to be in any way limiting.

It will be readily appreciated that the construction of the water chamber as described is simple to manufacture and each of the plastic components is itself capable of simple injection moulding. Consequently a water chamber according to the present invention is, while providing significant advantages, not significantly more expensive than existing chambers.

The invention claimed is:

1. An apparatus for use in humidified gases delivery treatment comprising:
   a housing,
   a pressurised gases supply within said housing,
   a pressurised gases outlet in said housing in fluid connection with said pressurised gases supply and adapted to make fluid connection with an inlet of a humidifier in order to provide gases flow to a said humidifier,
   a humidified gases return in said housing, adapted to make fluid connection with an outlet of a said humidifier in order to receive humidified gases from said humidifier,
   a patient outlet in said housing, in fluid connection with said humidified gases return in order to receive humidified gases from said humidified gases return and provide humidified gases to said patient outlet, said patient outlet being in fluid connection with or adapted to make fluid connection with a breathing conduit for delivery of humidified gases to a patient.

2. An apparatus for use in humidified gases delivery treatment as claimed in claim 1 wherein a said humidifier is a heatable water chamber, and said apparatus includes,
   a chamber heater connected to said housing and, said housing includes a humidifier engagement locating a said humidifier adjacent said chamber heater, said chamber heater adapted to vaporise liquid water in said water chamber in order to provide water vapour to said gases flow passing through said water chamber.

3. An apparatus for use in humidified gases delivery treatment as claimed in claim 2 wherein said water chamber has a base, and said water chamber is engagable with said humidifier engagement via a single motion, and said single motion of engagement urges the base of said water chamber adjacent and in contact with said chamber heater and makes a first fluid connection between said pressurised gases outlet and said humidifier inlet, and makes a second fluid connection between said humidified gases return and said humidifier outlet, with said first and second fluid connections being made in the direction of said single motion.

4. An apparatus for use in humidified gases delivery treatment as claimed in claim 3 wherein said pressurised gases outlet and said inlet of a said humidifier have between them first complementary male and female connectors, having a preferred insertion direction for completing a fluid connection by engagement of the mate and female connectors,
   said humidified gases return and said outlet of said humidifier have between them second complementary male and female connectors, having a preferred insertion direction for completing a fluid connection by engagement of the male and female connectors, said preferred insertion direction of said first connectors being the same as said preferred insertion direction of said second connectors, and being the same as at least the direction of a terminal part of said single motion.

5. An apparatus for use in humidified gases delivery treatment as claimed in claim 4 wherein said inlet of said humidifier and said outlet of said humidifier are each a female port,
   and said preastuised gases outlet and said humidified gases return are each a resilient tubular projection fitting within respective female ports with said water chamber engaged.

6. An apparatus for use in humidified gases delivery treatment as claimed in claim 5 wherein said tubular projections of said pressurised gases outlet and humidified gases return have substantially parallel axes of extension, said chamber heater includes a substantially planar heating plate, and said axes of extension of said tubes are at least substantially parallel with said insertion direction.

7. An apparatus for use in humidified gases delivery treatment as claimed in any one of claims 1–6 wherein said patient outlet includes a connector for receiving a breathing hose and at least one auxiliary electrical connection plug or socket or pneumatic connection plug or port, for a simultaneous connection when connecting a breathing circuit having complementary electrical or pneumatic connectors.

* * * * *

Disclaimer

7,111,624 B2 — Mohammad Thudor, Auckland (NZ); Ian Douglas Makinson, Auckland (NZ); Philip James Biggs, Auckland (NZ); Philip John Dickinson, Auckland (NZ). APPARATUS FOR DELIVERING HUMIDIFIED GASES. Patent dated September 26, 2006. Disclaimer filed December 12, 2016 by the assignee, Fisher & Paykel Healthcare Limited.

Hereby disclaim complete claims 1 and 2 of said patent.

*(Official Gazette, November 26, 2019)*